US006312681B1

(12) United States Patent
Engler et al.

(10) Patent No.: US 6,312,681 B1
(45) Date of Patent: *Nov. 6, 2001

(54) COMPOSITIONS AND METHODS FOR THE TREATMENT OF CANCER USING RECOMBINANT VIRAL VECTOR DELIVERY SYSTEMS

(75) Inventors: Heidrun Engler; Dan Maneval, both of San Diego, CA (US)

(73) Assignee: Canji Incorporated, San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,089

(22) Filed: Sep. 26, 1997

Related U.S. Application Data

(63) Continuation of application No. 08/584,077, filed on Jan. 11, 1996, now Pat. No. 5,789,244.

(51) Int. Cl.$^7$ .................................................. A61K 48/00
(52) U.S. Cl. ......................... 424/93.2; 424/93.1; 514/44; 435/455; 435/456
(58) Field of Search ................................. 514/44; 435/5, 435/6, 172.3, 320.1, 455, 456; 424/93.1, 93.2; 935/55, 57

(56) References Cited

U.S. PATENT DOCUMENTS 5,552,309 * 9/1996 March ................................. 435/172.3

FOREIGN PATENT DOCUMENTS

| WO93/00052 | 1/1993 | (WO) . |
| WO9510265 | 4/1995 | (WO) . |
| WO9711682 | 4/1997 | (WO) . |

OTHER PUBLICATIONS

Ross et al., "Gene therapy in the United States: A five–year status report", Hum. Gene Ther. 7 &: 1781–1790, Sep. 1996.*
Crystal, "Transfer of genes to humans: early lessons and obstacles to success", Science 270: 404–409, Oct. 1995.*
Verma et al., "Gene therapy—promises, problems and prospects", Nature 389: 239–242, Sep. 1997.*
Orkin et al., "Report and recommendations of the panel to assess the NIH investment in research on gene therapy", issued by the U.S. National Institutes of Health, Dec. 1995.*
Associated Press release, "One way to kill cancer: Give it a cold", accessed by PTO on World Wide Web at CNN.COM on May 22, 1997, May 20, 1997.*
Friedmann, "Gene therapy of cancer through restoration of tumor–suppressor functions?", Cancer 70: 1810–1817, 1992.* van Bueren et al., "Inactivation of human immunodeficiency virus type 1 by alcohols", J. Hosp. Infect. 28(2): 137–48. (Abstract only) Oct. 1994.*

Mazur et al., "Studies on the effect of some disinfectants on virus activity", Med. Dosw. Mikrobiol. 26(4): 331–337. (Abstract only), 1974.*

Tyler et al., "A surface test for virucidal activity of disinfectants: preliminary study with herpes virus", J. Hosp. Infect. 9(1): 22–29. (Abstract only) Jan. 1987.*

Culver et al., "Gene therapy for cancer", Trends in Genetics 10(5): 174–178, May 1994.*

Abe et al., "Transduction of a Drug–Sensitive Toxic Gene into Human Leukemia Cell Lines with a Novel Retroviral Vector (43611)", *Proc. Soc. Exp. Biol. Med.*, 2003:354–359 (1993).

Banerjee et al., "Changes in Growth and Tumorigenicity Following Reconstitution of Retinoblastoma Gene Function in Various Human Cancer Cell Types by Microcell Transfer of Chromosome 13", *Cancer Research*, 52:6297–6304 (1992).

Bass et al., "Recombinant Adenovirus–Mediated Gene Transfer to Genitourinary Epithelium In Vitro and In Vivo", *Cancer Gene Therapy*, 2(2) :97–104 (1995).

Blixt et al., "Enhancement of Intracellular Uncoating of Adenovirus in HeLa Cells in the Presence of Benzyl Alcohol as a Membrane Fluidizer", *Arch Virol*, 1299:265–277 (1993).

Brewster et al., *Eur. Urol.*, 25:177–182 (1994).

Cairns et al., "Loss of Heterozygosity at the RB Locus is Frequent and Correlates with Muscle Invasion in Bladder Carcinoma", *Oncogene*, 6:2305–2309 (1991).

*Cancer Facts and Figures*, 5–11 (1995).

Fujimoto et al., "Frequent Association of p53 Gene Mutation in Invasive Bladder Cancer", *Cancer Research*, 52:1393–1398 (1992).

Good et al., *Biochemistry*, 5:467 (1966).

Goodrich et al., "Expression of the Retinoblastoma Gene Product in Bladder Carcinoma Cell Associates with a Low Frequency of Tumor Formation", *Cancer Research*, 52:1968–1973 (1992).

(List continued on next page.)

Primary Examiner—Scott D. Priebe
(74) Attorney, Agent, or Firm—Townsend and Townsend and Crew LLP

(57) ABSTRACT

A method and pharmaceutical composition for the treatment of cancer using a gene delivery system, such as a viral vector delivery system, comprising a therapeutic gene wherein the gene delivery system is formulated in a buffer comprising a delivery-enhancing agent such as ethanol.

16 Claims, 6 Drawing Sheets

OTHER PUBLICATIONS

Li et al., *Human Gene Therapy*, 4:403–409 (1993).

Monson et al., "Indigocarmine as a Quantitative Indicator of Urothelial Integrity", *The Journal of Urology*, 145:842–845 (1992).

Morris et al., "Adenoviral–Mediated Gene Transfer to Bladder In Vivo", *J. Urology*, 152:506–509 (1994).

Parsons et al., "Bladder Surface Gycosaminoglycans: An Epithelial Permeability Barrier", *J. Urol.*, 143:139–142 (1990).

Rosenberg, Steven A., "The Immunotherapy and Gene Therapy of Cancer", *J. of Clinical Oncology*, 10 (2):180–200 (1992).

Spandidos et al., "Expression of the Normal H–rasl Gene Can Suppress the Transformed and Tumorigenic Phenotypes Induced by Mutant ras Genes", *Anticancer Research*, 10:1543–1554 (1990).

Takahashi et al., "The Retinoblastoma Gene Functions as a Growth and Tumor Suppressor in Human Bladder Carcinoma Cells", *Proc. Natl. Acad. Sci. USA*, 88:5257–5261 (1991).

Wills et al., "Development and Characterization of Recombinant Adenoviruses Encoding Human p53 for Gene Therapy of Cancer", *Human Gene Therapy*, 5:1079–1088 (19994).

Greney, et al., "characterization of limidazoline Binding Protein(s) Solubilized From Human Brainstem: Studies With [$^3$h]Idazoxan and [$^3$h]Clonidine." *Neurochem. Int.* 1994, pp. 183–191, vol. 25.

Harris M.P., et al. "Adenovirus–mediated p53 gene transfer inhibits growth of human tumor cells expressing mutant p53 protein." *Cancer Gene Therapy* 1996, pp. 121–130, vol. 3.

Pinnaduwage, et al., "Use of a quaternary amonium detergent in liposome mediated DNA transfection of mouse L–cells." *Biochimica et Biophysica Acta.* 1989, pp. 33–37, vol. 985.

* cited by examiner

| $10^7$ | $10^8$ | $10^9$ | $10^{10}$ | $10^{11}$ |
| FIG. 3A. | FIG. 3B. | FIG. 3C. | FIG. 3D. | FIG. 3E. |

COMPOSITIONS AND METHODS FOR THE TREATMENT OF CANCER USING RECOMBINANT VIRAL VECTOR DELIVERY SYSTEMS

This is a continuation of application Ser. No. 08/584,077, filed Jan. 11, 1996, now U.S. Pat. No. 5,789,244 the disclosure of which is incorporated by reference.

FIELD OF THE INVENTION

The present invention is directed to compositions and methods of treating cancer by gene therapy using a therapeutic gene, such as a tumor suppressor gene, delivered by a gene delivery system, such as a recombinant viral vector delivery system, formulated in a buffer comprising a delivery-enhancing agent. In particular, this invention relates to the delivery of the retinoblastoma tumor suppressor gene (RB) to cancerous epithelial tissues and organs, such as the bladder, using a recombinant adenoviral vector delivery system formulated in a buffer comprising a delivery-enhancing agent.

BACKGROUND OF THE INVENTION

Carcinoma of the bladder represents a significant source of morbidity and mortality. Bladder cancer ranks 10th in males and 12th in females in cancer related mortality (Cancer Facts and Figures (1995), Amer.Can.Soc. 5:11). Therapies available for the treatment of bladder cancer include adjuvant chemotherapy or immunotherapy, transurethral resection of superficial disease, radical cystectomy or radiotherapy which is often combined with systemic chemotherapy. Despite these therapeutic options, overall survival has not changed appreciably. (Ibid) Thus, new therapeutic modalities must be developed for the treatment of bladder cancer.

Gene therapy strategies have been developed as an alternative therapeutic approach (See for example, Brewster et al. *Eur Urol* (1994) 25:177–182; Takahashi et al., *Proc Natl Acad Sci USA* (1991) 88: 5257–5261; Rosenberg, SA, *J. Clin Oncol.* (1992) 10:180–199). Distinct approaches have been developed to treat neoplasms based on gene transfer methods. Methods have been developed to correct specific lesions at defined genetic loci which give rise to neoplastic transformation and progression (Spandidos et al., *Anticancer Res.* (1990) 10: 1543–1554; Banerjee et al. *Cancer Res.* (1992) 52:6297–6304). Overexpression of dominant oncogenes may be addressed using techniques to inhibit the transforming gene or gene product. Loss of tumor suppressor gene function may be approached using methods to reconstitute wild-type tumor suppressor gene function (Goodrich et al., *Cancer Res.* (1992)52:1968–1973). Besides these methods to achieve mutation compensation, genetic techniques have been developed to specifically and selectively eradicate tumor cells. These approaches of molecular chemotherapy rely on specific expression of toxin genes in neoplastic cells (Abe et al., *Proc Soc Exp Biol Med.* (1993) 203: 354–359). Finally, gene transfer methods have been used to achieve antitumor immunization. These methods of genetic immunopotentiation use techniques of genetic immunoregulation to enhance immune recognition of tumors. Consequently, a variety of distinct approaches have been developed to accomplish gene therapy of cancer.

A high incidence of mutations has been observed in tumor suppressor genes, such as p53 and RB, in the case of carcinoma of the bladder (Fujimoto et al. *Cancer Res.* (1992) 521393–1398; Cairns et al. *Oncogene* (1991) 6:2305–2309). For such genetic lesions of tumor suppressor genes, reversion of the neoplastic phenotype can be demonstrated with replacement of the corresponding wild-type tumor suppressor gene. (Spandidos, Id.; Banerjee, Id.)

In vitro studies using cell lines derived from human bladder tissues have demonstrated efficient transgene expression following infection with recombinant adenovirus (Bass et al.(1995) *Cancer Gene Therapy* 2:2: 97–104). Experiments in vivo have also shown adenovirus transgene expression in the urinary bladder of rodents after intravesical administration (Ibid;Morris et al.(1994) *J. Urology.* 152: 506–50). In vitro experiments with wild-type adenovirus demonstrate that virus attachment and internalization is not influenced by benzyl alcohol, but do demonstrate an enhanced uncoating of the virion (Blixt et al. (1993) *Arch. Virol.* 129:265–277). In vivo efforts with agents (e.g. acetone, DMSO, protamine sulfate) can break down the protective "mucin" layer that protects the bladder epithelium from bacteria, viruses and other pathogens (Monson et al. (1992) *J. Urol.* 145:842–845; Parsons et al. (1990) *J. Urol.* 143:139–142). None of the methods tried to date achieve enhanced delivery of a therapeutic tumor suppressor gene to the bladder for the treatment of bladder cancer. In order to accomplish gene therapy for treatment of bladder cancer, gene therapy methods must be developed to accomplish direct, optimal, in vivo tumor suppressor gene delivery to the bladder epithelium.

An object of the present invention is to provide a therapeutic composition for optimal delivery of a therapeutic gene, such as a tumor suppressor gene, to suppress the neoplastic phenotype of cancer cells. Another object of this invention is to provide a means of enhanced delivery of a therapeutic gene, such as a tumor suppressor gene, to cancerous tissues and organs using a gene delivery system, such as a recombinant viral vector delivery system, formulated in a buffer comprising a delivery-enhancing agent. Yet another object of this invention is to provide a method of treating cancer of the bladder by gene therapy using a therapeutic gene, such as a tumor suppressor gene, delivered by a recombinant adenoviral vector delivery system formulated in a buffer comprising a delivery-enhancing agent. Still another object of this invention is to enable adequate delivery of a tumor suppressor gene to cancer cells in the bladder to insure transfer and ultimately expression of therapeutic gene in the cancerous bladder epithelium. Still another object of this invention is to provide a method of treating cancer of an epithelial tissue or organ by gene therapy using a therapeutic gene delivered by a gene delivery system formulated in a buffer comprising the delivery enhancing agent ethanol.

SUMMARY OF THE INVENTION

The objects of this invention are accomplished by enhanced delivery of a therapeutic gene, such as a tumor suppressor gene, contained within a gene delivery system, such as a recombinant viral vector delivery system, wherein the recombinant viral vector delivery system is formulated in a buffer comprising a delivery-enhancing agent, such as an alcohol. A therapeutically effective amount of a therapeutic gene contained within a recombinant viral vector delivery system formulated in a buffer comprising a delivery-enhancing agent, such as an alcohol, is useful for the treatment of cancer of certain epithelial tissues and organs, such as the bladder. For the first time in this invention, it was discovered that a recombinant viral vector delivery system, such as an adenoviral vector delivery system, formulated in a buffer comprising a delivery-enhancing agent, such as ethanol, enhances delivery of a therapeutically effective dose of a therapeutic gene, such as a tumor suppressor gene, to a cancerous epithelial tissue or organ, such as the bladder epithelium. It was not appreciated until the instant invention that formulation of a gene delivery system, such as a recombinant viral vector delivery system, in a buffer containing a delivery-enhancing agent, such as ethanol, results in enhanced transfer and ultimately expression of a therapeutic gene in the cancerous bladder epithelium. Accordingly, in one aspect the invention is directed to a therapeutic composition comprising a gene delivery system, such as a recombinant viral vector delivery system, comprising a therapeutic gene, such as the retinoblastoma tumor suppressor gene, wherein the gene delivery system is formulated in a buffer comprising a delivery-enhancing agent to treat bladder cancer. Yet another aspect of the invention is directed to a therapeutic composition comprising a gene delivery system, such as a recombinant viral vector delivery system, comprising a therapeutic gene, such as the retinoblastoma tumor suppressor gene, wherein the gene delivery system is formulated in a buffer comprising a delivery-enhancing agent, ethanol, to treat cancer of an epithelial tissue or organ. In another aspect the invention is directed to a method of treating cancer of epithelial tissues and organs, such as the bladder, through the use of such compositions.

DETAILED DESCRIPTION

Figure 1:
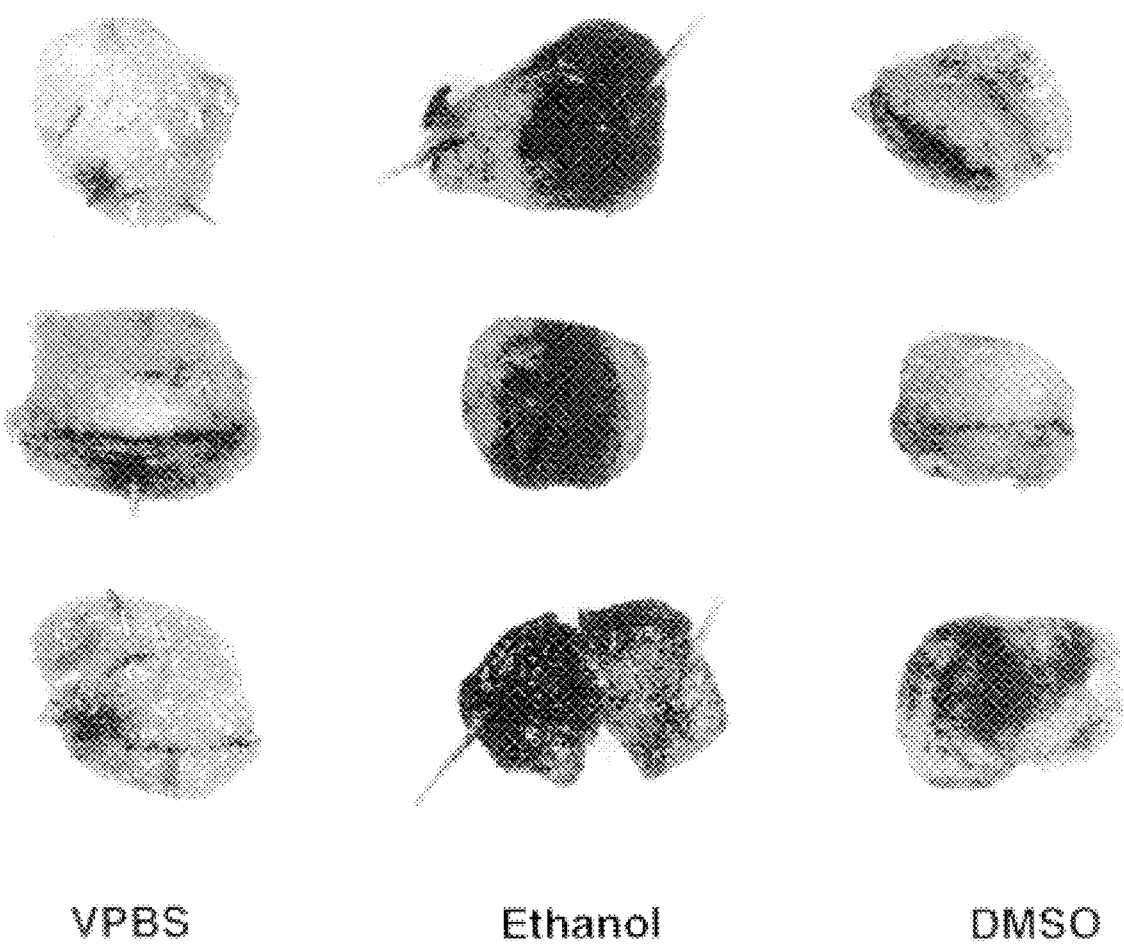
FIG. 1. Formulation influences adenovirus mediated gene transfer in the rat bladder epithelium after intravesical administration. Rats received a single intravesical 0.25 ml bolus of rAd-βgal in ($1.7 \times 10^{11}$ PN/mL) diluted in VPBS (2% sucrose, 2 mM $MgCl_2$ in PBS) (left column), 30% ethanol (center column), or 50% DMSO (right column). Animals were sacrificed 2 days later. Bladders were fixed, and whole organs were stained with an X-gal solution and photographed. Hydrolysis of X-gal by β-galactosidase results in a blue color that localized to the superficial luminal bladder epithelium. The rAd-βgal diluted in 30% ethanol improved gene expression, evidenced by increased blue staining. No staining was detected in bladder tissue from an untreated control animal.

As used herein, "a gene delivery system" refers to any means of delivery of a therapeutic gene to a particular epithelial tissue or organ including, for example, viral vectors and non-viral vectors. Examples of non-viral vectors are any lipid based, lipid encapsulated DNA or cationic lipid/DNA complexes. Examples of viral vectors are vectors of viruses, such as herpes virus, retrovirus, vaccinia virus and adenovirus. In one preferred embodiment a gene delivery system is a "recombinant viral vector delivery system" refers to recombinant viruses capable of delivery of therapeutic tumor suppressor genes to a particular tissue or organ. "Recombinant" refers to the progeny resulting from the adenoviral vector constructed using the means and methods of recombinant technology. A preferred recombinant viral vector is the adenoviral vector delivery system which has a deletion of the protein IX gene (See International Patent Application WO 95/11984, which is herein incorporated by reference).

The recombinant adenoviral vector delivery system comprising a therapeutic gene, such as a tumor suppressor gene, is formulated in a buffer comprising a delivery-enhancing agent. "A delivery-enhancing agent" refers to any agent which enhances delivery of a therapeutic gene, such as a tumor suppressor gene to a cancerous tissue or organ.

Such enhanced delivery may be achieved by various mechanisms. One such mechanism may involve the disruption of the protective glycosaminoglycan layer on the epithelial surface of the bladder.

Examples of such delivery-enhancing agents are alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconol acetate, and sodium acetate are further examples of delivery-enhancing agents. Hypertonic salt solutions liken 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethylenglycol 400, polysorbate 80, polyoxyethylene ethers, polyglycol ether surfactants and DMSO. Bile salts such as taurocholate, sodium tauro-deoxycholate, eoxycholate, chenodesoxycholate, glycocholic acid, glycochenodeoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used.

In one embodiment, the delivery-enhancing agent is included in the buffer in which the recombinant adenoviral vector delivery system is formulated.

In the case of a pharmaceutical composition comprising a tumor suppressor gene contained in a recombinant adenoviral vector delivery system formulated in a buffer which further comprises a delivery-enhancing agent, the pharmaceutical composition may be administered over time in the range of about 5 minutes to 2 hours, preferably 10 minutes to 90 minutes, and most preferably 15 minutes to 60 minutes. In another embodiment the delivery-enhancing agent may be administered prior to administration of the recombinant adenoviral vector delivery system containing the tumor suppressor gene. The prior administration of the delivery-enhancing agent may be in the range of about 30 seconds to 1 hour, preferably 1 minute to 10 minutes, and most preferably 1 minute to 5 minutes prior to administration of the adenoviral vector delivery system containing the tumor suppressor gene. The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v).

The buffer containing the delivery-enhancing agent may be any pharmaceutical buffer such as phosphate buffered saline or sodium phosphate/sodium sulfate, tris buffer, glycine buffer, sterile water and other buffers known to the ordinarily skilled artisan such as those described by Good et al. (1966) *Biochemistry* 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

The term "enhanced" describes the increased delivery of the therapeutic gene, such as a tumor suppressor gene, to the cancerous tissue or organ. Increased delivery of a therapeutic gene, such as a tumor suppressor gene, can be measured by various means, for example by measuring expression of the tumor suppressor gene compared to expression levels when the tumor suppressor gene is delivery in an adenoviral vector delivery system in a buffer lacking the delivery-enhancing agent.

Examples of therapeutic genes are tumor suppressor genes and the suicide gene thymidine kinase. Examples of tumor suppressor genes are the retinoblastoma gene, either full length ($p110^{RB}$) or retinoblastoma gene encoding mutant retinoblastoma proteins such as ($p94^{RB}$ or $p56^{RB}$), mitosin, H-NUC, and p53. The composition of this invention comprises a therapeutically effective amount of a therapeutic gene, such as a tumor suppressor gene, contained in a recombinant viral vector delivery system in a buffer comprising a delivery-enhancing agent. Therapeutically effective amounts of the pharmaceutical composition comprising a therapeutic gene, such as the retinoblastoma tumor suppressor gene, in a recombinant viral vector delivery system formulated in a buffer comprising a delivery-enhancing agent will be administered in accord with the teaching of this invention. For example, therapeutically effective amounts of the retinoblastoma tumor suppressor gene in the recombinant adenoviral vector delivery system formulated in a buffer containing a delivery-enhancing agent are in the range of about $1 \times 10^7$ particles/ml. to $1 \times 10^{12}$ particles/ml. A preferred therapeutically effective amount of the retinoblastoma tumor suppressor gene in the recombinant adenoviral vector delivery system formulated in a buffer containing a delivery-enhancing agent is in the range of about $1 \times 10^9$ particles/ml to $1 \times 10^{11}$ particles/ml. A most preferred therapeutically effective amount of the retinoblastoma tumor suppressor gene in the recombinant adenoviral vector delivery system formulated in a buffer containing a delivery-enhancing agent is in the range of about $5 \times 10^9$ particles/ml to $5 \times 10^{10}$ particles/ml.

The composition of this invention may additionally include a stabilizer, enhancer or other pharmaceutically acceptable carriers or vehicles. A pharmaceutically acceptable carrier can contain a physiologically acceptable compound that acts, for example, to stabilize the recombinant adenoviral vector delivery system comprising the tumor suppressor gene. A physiologically acceptable compound can included, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physio-chemical characteristics of the recombinant adenoviral vector delivery system and the particular tumor suppressor gene contained therein. Examples of carriers, stabilizers or adjuvants can be found in Martin, *Remington's Pharm. Sci.*, 15th Ed. (Mack Publ. Co., Easton, Pa. 1975), incorporated herein by reference.

The recombinant viral vector delivery system comprising a therapeutic gene formulated in a buffer comprising a delivery-enhancing agent may be delivered to any cancerous tissue or organ using any delivery method known to the ordinarily skilled artisan for example, intratumoral or intravesical administration. Cancerous tissues and organs include any tissue or organ having an epithelial membrane such as the gastro-intestinal tract, the bladder, respiratory tract, and the lung.

The following examples are intended to illustrate, not limit the scope of this invention.

EXAMPLE 1

Ethanol Improves Gene Transfer in the Bladder

Initial experiments have shown that several factors including virus concentration, time of administration, and volume of dosing can influence gene transfer to the bladder epithelium after intravesical administration to rats. Because increased penetration of dyes can be achieved by intravesical administration of different solvents, modification of the adenovirus formulation was also investigated as an alternative strategy to increase adenovirus transgene expression in the bladder (Monson et al. (1991) *Urology* 145:842–845). The instant experiments focused on the use of ethanol to increase adenovirus transgene expression in the bladder.

Nine female buffalo rats (Harlan Sprague Dawley) were anesthetized with isoflurane and received a single intravesical administration of a human recombinant adenovirus encoding the lacZ gene (rAd-βgal). The human recombinant adenoviral vector comprising the lacZ gene (rAd-βgal) is described in Wills et al. (1994) *Human Gene Therapy* 5:1079–1088. Before instillation bladders were flushed with PBS and emptied. rAd-βgal was then diluted to achieve a final concentration of $1.7 \times 10^{11}$ PN/mL in 1) VPBS (2% (w/v) sucrose and 2 mM MgCl$_2$ in PBS), 2) 30% (v/v) ethanol, or 3) 50% (v/v) DMSO, and instilled in a 250 µL volume (N=3 animals/group). The administered material was retained in the bladder for 45 minutes. The bladder were then flushed with PBS, and the animals were permitted to recover from the procedure. Two days after administration, rats were sacrificed, bladders were harvested, fixed, and whole organs were stained with an X-gal solution to evaluate reporter gene transfer. X-gal stained tissues were then paraffin embedded, sectioned, and counter stained with hematoxylin and eosin.

Figure 2:
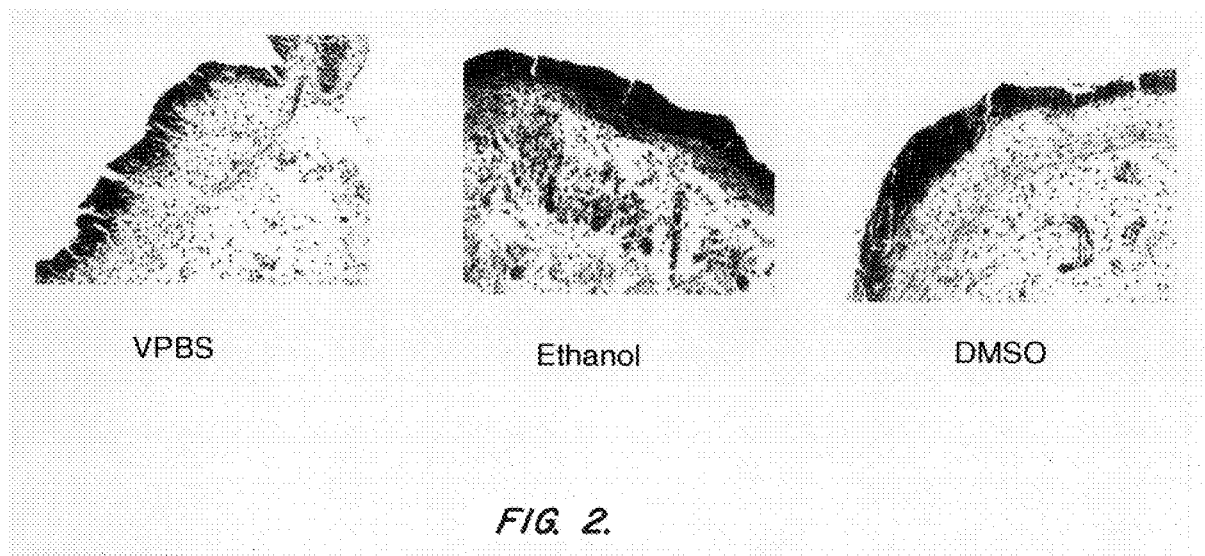
FIG. 2. Adenovirus transgene expression in bladder epithelial cells. Bladder specimens described in FIG. 1 were embedded, sectioned, and counter stained with hematoxylin and eosin. β-galactosidase expression (blue staining) was detected primarily in the epithelial cells, and was dramatically increased when the delivery-enhancing agent, ethanol, was added to the formulation. Inflammatory cells were not detected in the tissue.

Transgene expression, consequent to delivery by the adenoviral vector, was detected in bladders from all animals treated with rAd-βgal but not in an untreated control. Transgene expression was similar to previously published results using the PBS/sucrose formulation (Bass et al. (1995) *Cancer Gene Therapy* 2:2:97–104). In sharp contrast, β-galactosidase expression in the luminal epithelial surface was greatly enhanced in animals that received rAd-βgal diluted in 30% ethanol (FIG. 1). Histologic evaluation of the bladder tissue also demonstrated increased β-galactosidase expression of the transitional bladder epithelium when ethanol was added to the adenovirus formulation (FIG. 2). The interaction of ethanol with the protective glycosaminoglycan (GAG) layer on the epithelium surface provides a mechanism for the observed increase in transgene expression. Disruption of this layer may facilitate virus-cell interaction at the surface and potentially enhance penetration into the sub mucosa.

EXAMPLE 2

Dose-Dependent Transgene Expression in the Rat Bladder

Figure 3:
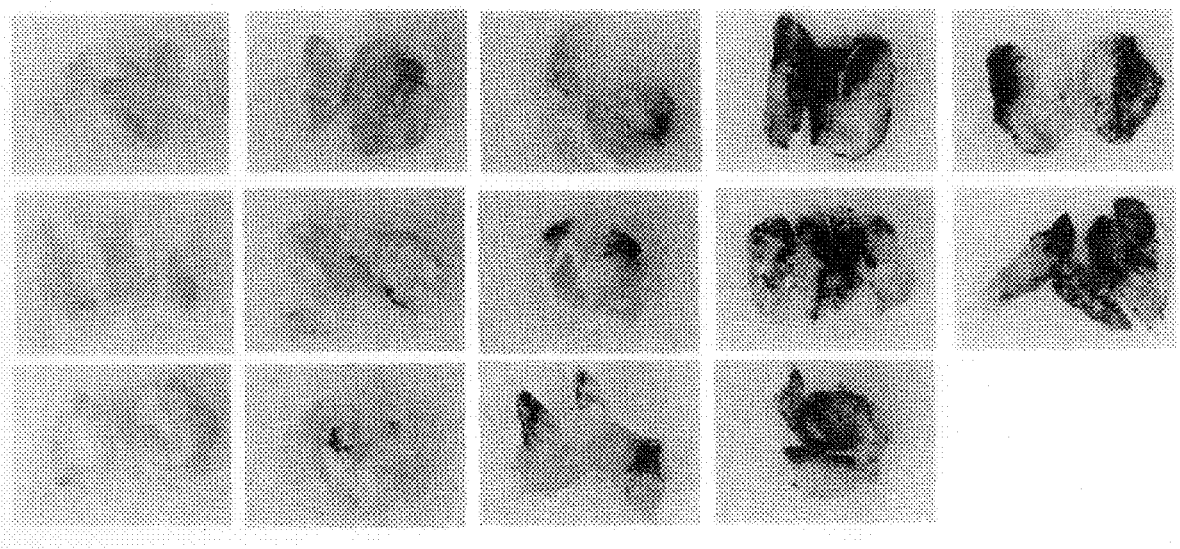
FIG. 3. Dose dependent adenovirus transgene expression in the rat bladder after intravesical administration. Rats received a single intravesical bolus of rAd-βgal (concentrations ranging from $2 \times 10^7$ to $2 \times 10^{11}$ PN/mL) diluted in 30% (v/v) ethanol in 0.5 ml. Animals were sacrificed two days later. Bladders were fixed, and whole organs were stained with an X-gal solution. Hydrolysis of X-gal by β-galactosidase results in a blue color that can be localized on the superficial luminal bladder epithelium. The extent of transgene expression correlated with the concentration of the administered recombinant adenovirus, with no evidence of expression at the lowest concentration.

In another experiment, 18 female Sprague-Dawley rats were anaesthetized with isoflurane and received a single 0.5 ml intravesical bolus of rAd-βgal at concentrations of $2 \times 10^7$, $2 \times 10^9$, $2 \times 10^9$, $2 \times 10^{10}$, and $2 \times 10^{11}$ PN/mL in a 22.5% (v/v) ethanol formulation. After a 45 minute incubation, the bladders were flushed with PBS, and animals were permitted to recover from anesthesia. Two days later, animals were sacrificed, and bladders were harvested, fixed, and whole organs were stained with X-gal solution to evaluate adenovirus transgene expression. β-galactosidase expression in the luminal bladder epithelium correlated with dose (FIG. 3). No striking differences were observed among animals receiving $2 \times 10^{10}$ or $2 \times 10^{11}$ PN/mL, suggesting a saturation of transgene expression in this model. Analysis of the volume voided after instillation indicated only a minimal reduction in the infectious titer of the dosing material at these high doses. Expression of β-galactosidase decreased at lower concentrations. No evidence of β-galactosidase expression was detected in animals dosed at a concentration of $1 \times 10^7$ PN/mL or in an untreated control animal.

EXAMPLE 3

ACNRB Gene Transfer in the Mouse Bladder

Figure 4:
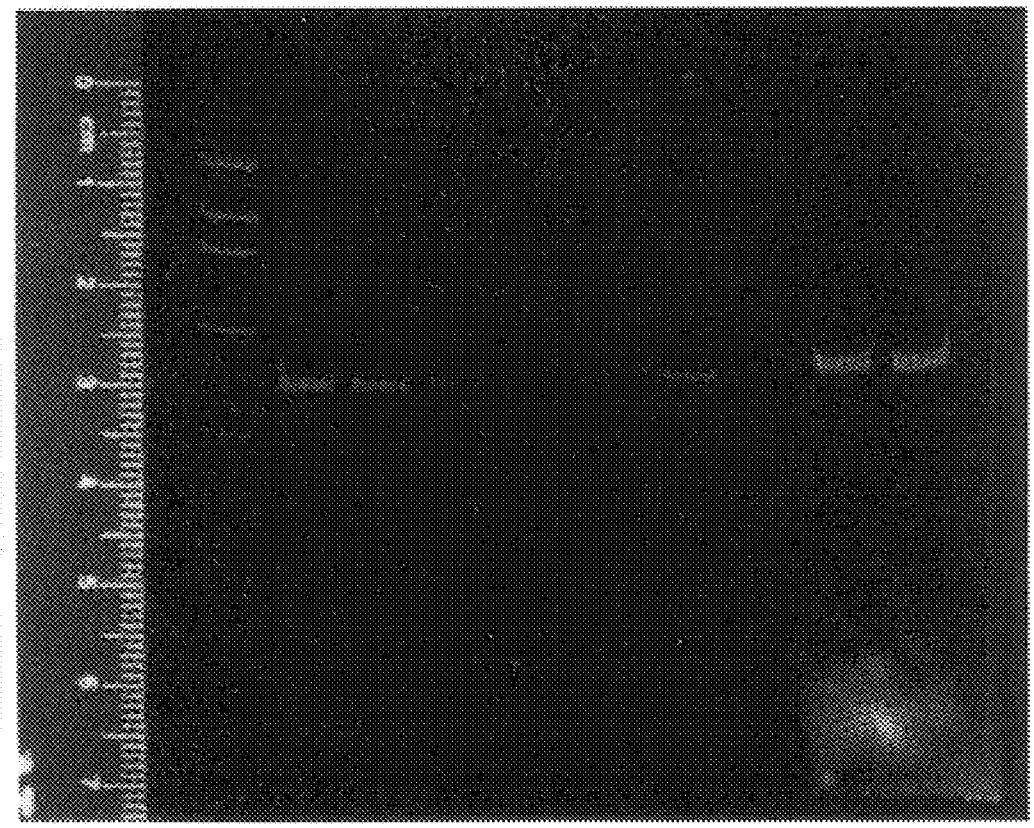
FIG. 4. RT-PCR analysis of ACNRB expression in the mouse bladder after intravesical administration. Mice received a single 80 μL intravesical bolus of ACNRB ($4 \times 10^{10}$ PN/ml) diluted in a VPBS solution or a 30% (v/v) ethanol solution. Animals were sacrificed 48 hours later, and bladders, livers, and kidneys were harvested. Tissues were homogenized, and total RNA was extracted using TRI-Reagent®. An aliquot of total RNA was analyzed by an RT-PCR assay. Primers were generated to identify ACNRB and amplify the region from the 3' end of the CMV sequence and to the 5' end of the RB sequence. Following amplification (30 cycles) RT-PCR products were separated on a 10% polyacrylamide gel, stained with ethidium bromide, and photographed. Increased ACNRB expression was detected after treatment with ACNRB in 30% (v/v) ethanol compared to very low expression after treatment with ACNRB in VPBS. Positive controls for the assay included samples from ACNRB-infected 5637 human bladder cancer cells (CONTROL). Bladder RNA samples from ACNRB-infected animals that were amplified with primers specific for beta-actin provided an internal control for the quality of RNA. Untreated samples and bladder samples without the reverse transcriptase (RT) provided controls for contaminating DNA.

A pilot study was conducted to specifically evaluate expression of the RB transgene using a RT-PCR assay. Eight female ICR mice (Charles River Laboratories) were anesthetized with avertine and each received a single 80 µL intravesical administration of a human recombinant adenovirus encoding RB (ACNRB). ACNRB ($4 \times 10^{11}$ PN/mL) was diluted and prepared in a PBS solution or a 30% (v/v) ethanol solution. After the virus was retained in the bladder for 45 minutes, the animals were permitted to recover and void. Mice were sacrificed 2 days or 14 days after ACNRB administration, and bladders, livers, and kidneys from each animal were harvested, homogenized, and processed for analysis (N=2 animals/group). Transgene expression was determined using RT-PCR with a primer specific for ACNRB. Two days after dosing, levels of ACNRB expression in the bladder homogenates were detected from animals that received ACNRB prepared in 30% ethanol (FIG. 4). No evidence of expression was detected in non-bladder tissue or in any samples collected 14 days after dosing.

EXAMPLE 4

Kinetics Of Biodistribution and ACNRB Expression After Intravesical Administration to Mice To investigate the time course of expression after intravesical administration, 40 female mice (Charles River Laboratories) were anaesthetized with avertine and received a single 80 μL bolus of ACNRB ($4 \times 10^{10}$ PN/mL in 22% (v/v) ethanol). The instilled material was retained in the bladder for approximately 45 minutes, and animals were permitted to recover from the procedure. Mice were sacrificed 1, 2, 3, 4, 5, 6, 7, and 14 days after administration (N=4/time) for analysis. Bladders, livers, and kidneys were harvested and snap frozen in liquid nitrogen for subsequent analysis. For detection of ACNRB expression, tissue samples were homogenized, and total RNA was extracted using TRI-Reagent®. An aliquot of total RNA was amplified in an RT-PCR assay using primers specific for ACNRB to distinguish transgene expression from endogenous expression. For detection of ACNRB DNA, a DNA extraction kit (Stratagene) was used on tissue homogenates. PCR was performed with the primers specific for ACNRB, as described above for the RT-PCR analysis.

Figures 5A, 5B, 5C:
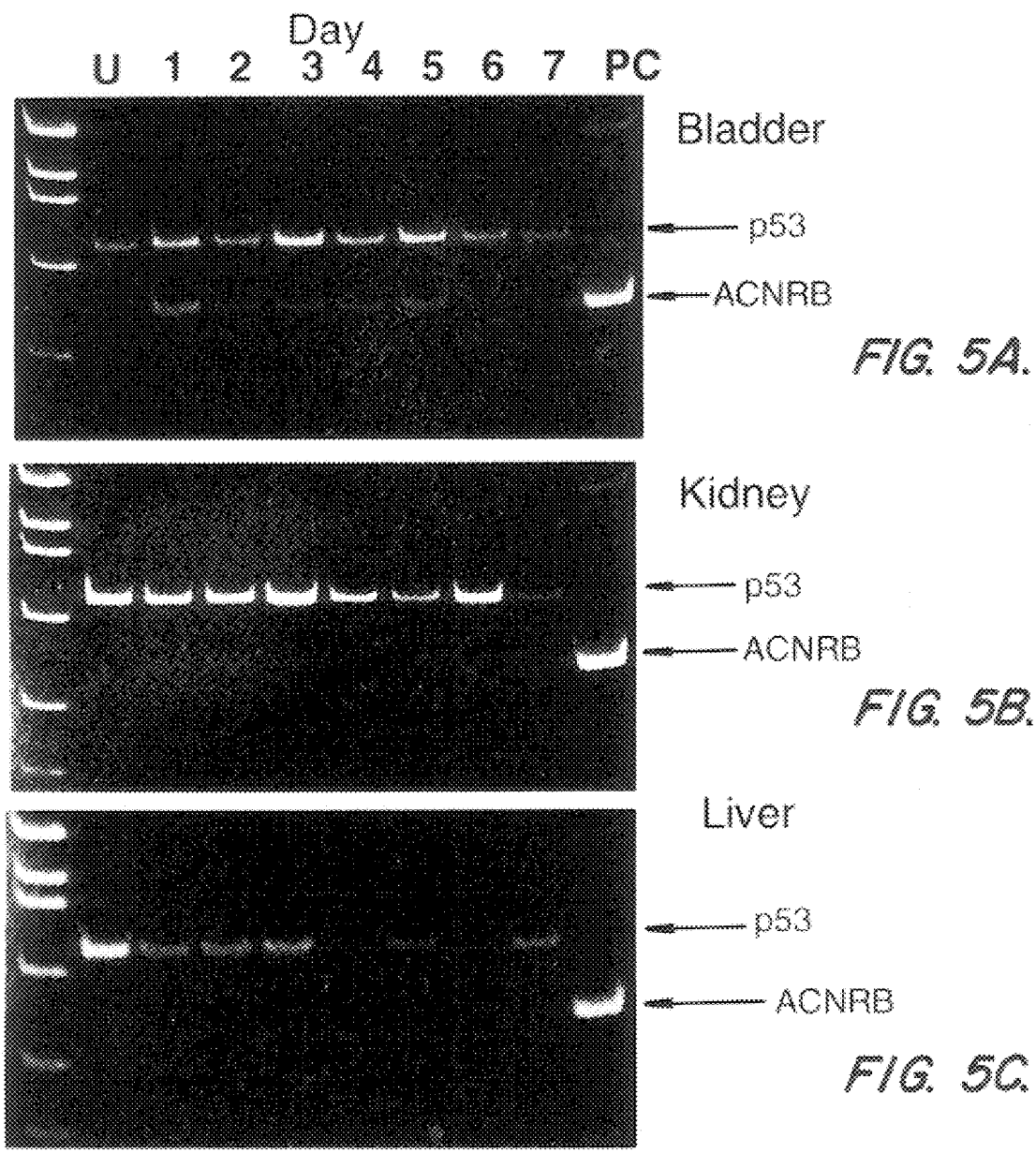
FIG. 5. Time course of ACNRB expression in bladder, kidney, and liver tissue after intravesical administration of ACNRB. Mice received a single 80 ML intravesical bolus of ACNRB ($4 \times 10^{10}$ PN/mL) in a 22% (v/v) ethanol solution. Animals were sacrificed 1, 2, 3, 4, 5, 6, 7, and 14 days later, and bladders, kidneys, and livers were harvested. Tissues were homogenized (N=2/time), and total RNA was extracted from a sample using TRI-Reagent®. An aliquot of total RNA was analyzed using an RT-PCR assay. Primers were designed to identify ACNRB and amplify the region from the 3' end of the CMV sequence and to the 5' end of the RB sequence. A set of primers for the mouse p53 gene spanning exons 4 to 6 was used as an internal control for each reaction. Following amplification (30 cycles) RT-PCR products were separated on a 10% polyacrylamide gel, stained with ethidium bromide, and photographed. A parallel reaction without reverse transcriptase was performed for each sample to test for potential DNA contamination. ACNRB expression was detected from bladder tissue samples harvested 1 to 6 days post injection, but not in samples collected on days 7 or 14 (upper panel). Minimal levels of ACNRB expression were detected in kidney homogenates collected only on days 1, 2, and 3 (middle panel). In contrast, no evidence for ACNRB expression was measured in liver samples collected during the 2-week interval (lower panel). Samples from an untreated animal (U) and from ACNRB-treated bladder cells (PC) were used as negative and positive controls, respectively.

ACNRB transgene expression in the bladder omogenates was detected only in samples collected on days 1–6, with expression relative to endogenous p53 decreasing with time (FIG. 5, upper panel). No expression was detected from samples collected 7 and 14 days after administration. Interestingly, some ACNRB expression was detected in the kidneys on days 1, 2 and 3, but no expression was observed in the liver (FIG. 5, lower panels).

Figure 6A:
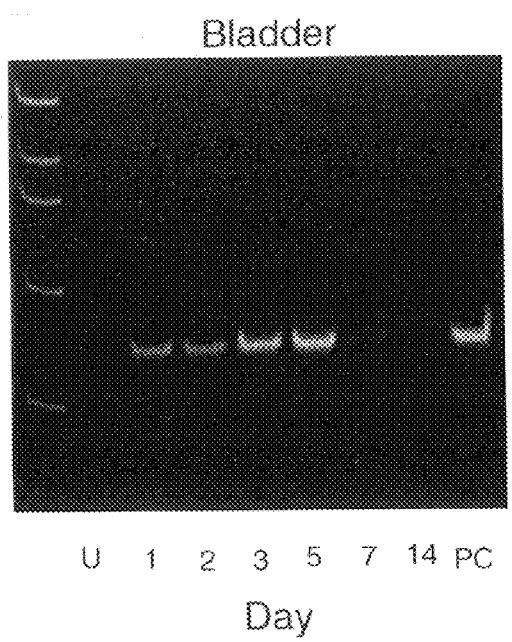
FIG. 6. ACNRB DNA in bladder and kidney homogenates after intravesical administration. Mice received a single 80 μL intravesical bolus of ACNRB ($4 \times 10^{10}$ PN/mL) in a 22% (v/v) ethanol). Animals were sacrificed 1, 2, 3, 4, 5, 6, 7, and 14 days later, and kidneys and livers were harvested. Tissues were homogenized (N=2/time), and total DNA was extracted. An aliquot of total DNA was then analyzed in a PCR assay using primers to identify ACNRB and amplify the region from the 3' end of the CMV sequence and to the 5' end of the RB sequence. Following amplification (30 cycles) PCR products were separated on a 10% polyacrylamide gel, stained with ethidium bromide, and photographed. DNA was detected in all of the bladder homogenates collected during the 2-week study (left panel). ACNRB DNA was also detected in kidney samples collected from day 1 to day 7, but not in samples collected on day 14 (right panel). No evidence for ACNRB DNA was detected in liver samples harvested during the study (data not shown). Samples from an untreated animal (U) and purified ACNRB DNA (PC) were used as negative and positive controls, respectively.
Figure 6B:
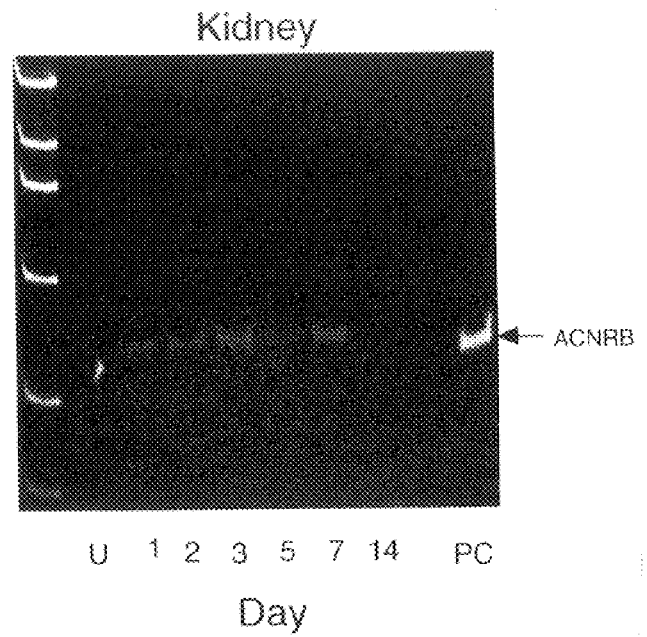

ACNRB DNA was detected in bladder tissue of all animals that received ACNRB, including those harvested 14 days after administration. DNA was also recovered from the kidney homogenates, consistent with the ACNRB expression detected in this tissue (FIG. 6). In contrast, no ACNRB DNA was detected in the livers of mice that received an intravesical dose of the recombinant adenovirus.

Because systemic administration of recombinant adenovirus results primarily in transgene expression in the liver (Li et al. (1993) *Human Gene Therapy* 4:403–409), the absence of ACNRB DNA and expression in liver samples (FIGS. 5 and 6) suggests negligible systemic exposure of ACNRB after intravesical administration. Retrograde flow via the ureters may have contributed to the detection of ACNRB in the kidney.

The data presented above demonstrate transgene expression in the rodent bladder following intravesical administration of ACNRB. These studies further indicate that adenovirus-mediated gene transfer to the bladder epithelium can be enhanced by the presence of a delivery-enhancing agent, such as ethanol, in the formulation. One mechanism for the increased gene transfer may be the disruption of the protective glycosaminoglycan layer on the epithelial surface of the bladder. A single intravesical administration of ACNRB in a 20–30% (v/v) ethanol formulation results in transgene expression in the bladder that persists for. approximately one week. Retrograde ureteral flow provides a likely explanation for the transient expression of ACNRB detected in the kidney. The absence of ACNRB expression and ACNRB DNA in the liver indicates limited systemic exposure after intravesical administration.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, for example to formulate the recombinant adenoviral vector delivery system in a buffer containing a delivery-enhancing agent for treating other cancers, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A method for delivering an adenoviral vector which comprises a transgene to a cancer cell in the epithehial membrane of a bladder, the method comprising administering to the epithelial membrane the adenoviral vector and between 1% and 50% (v/v) ethanol, wherein the adenoviral vector infects the cell and the transgene is expressed in infected cells.

2. The method of claim 1 wherein the adenoviral vector has a deletion of the protein IX gene.

3. The method of claim 1 wherein the concentration of ethanol is in the range of 10% to 40% (v/v).

4. The method of claim 1 wherein the concentration of ethanol is in the range of 15% to 30% (v/v).

5. The method of claim 1, wherein the adenoviral vector and ethanol are administered over a time of 5 minutes to 2 hours.

6. The method of claim 1, wherein the adenoviral vector and ethanol are administered over a time of 10 minutes to 90 minutes.

7. The method of claim 1, wherein the adenoviral vector and ethanol are administered over a time of 15 minutes to 60 minutes.

8. The method of claim 1, wherein the transgene is a tumor suppressor gene.

9. The method of claim 8, wherein the tumor suppressor gene encodes p53, $p110^{RB}$, or $p56^{RB}$.

10. The method of claim 1, wherein the ethanol is administered prior to administration of the adenoviral vector.

11. The method of claim 10, wherein the ethanol is administered 30 seconds to 1 hour prior to administration of the adenoviral vector.

12. The method of claim 10, wherein the ethanol is administered 1 minute to 10 minutes prior to administration of the adenoviral vector.

13. The method of claim 10, wherein the ethanol is administered 1 minute to 5 minutes prior to administration of the adenoviral vector.

14. The method of claim 1, wherein the adenoviral vector is formulated in a buffer comprising ethanol.

15. The method of claim 1, wherein the transgene encodes β-galactosidase.

16. The method of claim 1, wherein the adenoviral vector is administered to the epithelial membrane intravesically.

* * * * *

UNITED STATES PATENT AND TRADEMARK OFFICE
CERTIFICATE OF CORRECTION

PATENT NO. : 6,312,681 B1
DATED : November 6, 2001
INVENTOR(S) : Engler et al.

It is certified that error appears in the above-identified patent and that said Letters Patent is hereby corrected as shown below:

<u>Column 10,</u>
Line 17, please delete the word "epithehial" and insert therefor -- epithelial --

Signed and Sealed this

Fourth Day of June, 2002

Attest:

JAMES E. ROGAN
Attesting Officer     Director of the United States Patent and Trademark Office